(12) United States Patent  
Cragg

(10) Patent No.: US 6,387,122 B1
(45) Date of Patent: *May 14, 2002

(54) INTRALUMINAL STENT AND GRAFT

(75) Inventor: Andrew H. Cragg, Edina, MN (US)

(73) Assignee: Boston Scientific Technology, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/687,247

(22) Filed: Oct. 13, 2000

Related U.S. Application Data

(63) Continuation of application No. 09/251,964, filed on Feb. 16, 1999, which is a continuation of application No. 09/005,654, filed on Jan. 12, 1998, now abandoned, which is a continuation of application No. 08/478,181, filed on Jun. 7, 1995, now Pat. No. 5,766,237, which is a division of application No. 08/344,524, filed on Nov. 23, 1994, now Pat. No. 5,683,448, which is a continuation of application No. 08/025,957, filed on Mar. 3, 1993, now abandoned, which is a continuation-in-part of application No. 07/839,911, filed on Feb. 21, 1992, now Pat. No. 5,405,377.

(51) Int. Cl.⁷ .................................................. A61F 2/06
(52) U.S. Cl. ..................................... 623/1.16; 623/1.15
(58) Field of Search ............................. 623/1.12, 1.11, 623/1.15, 1.18, 1.19, 1.2, 1.22, 1.42, 1.45, 1.46; 606/108, 191, 194; 608/198

(56) References Cited

U.S. PATENT DOCUMENTS 5,019,090 A * 5/1991 Pinchuk ........................ 623/1
5,035,706 A * 7/1991 Gianturco et al. .......... 606/198

* cited by examiner

Primary Examiner—David O. Reip
Assistant Examiner—Vy Q. Bui
(74) Attorney, Agent, or Firm—Ratner & Prestia

(57) ABSTRACT

An intraluminal stent and graft includes a stent made of a continuous helix of zig-zag wire and loops which connect adjacent apices of the wire. The stent is compressible and self-expandable substantially to a pre-compressed configuration. The device also includes a graft secured to the stent and made of a suitable biocompatible material.

15 Claims, 3 Drawing Sheets

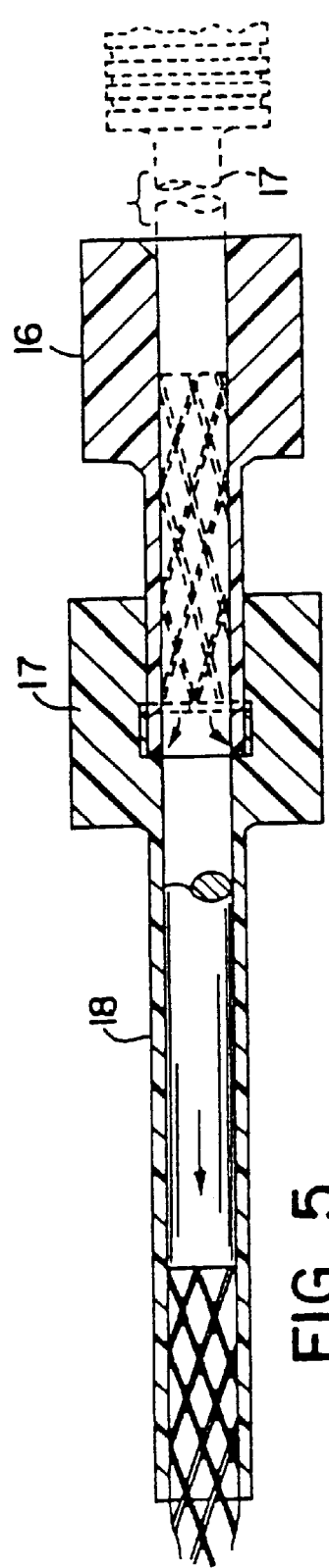
FIG. 5
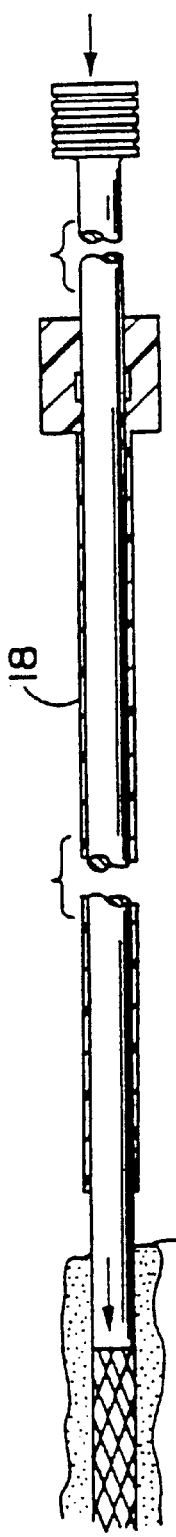
FIG. 6
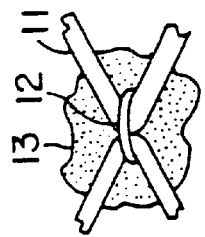
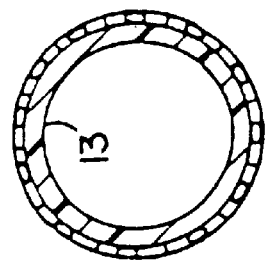
FIG. 8
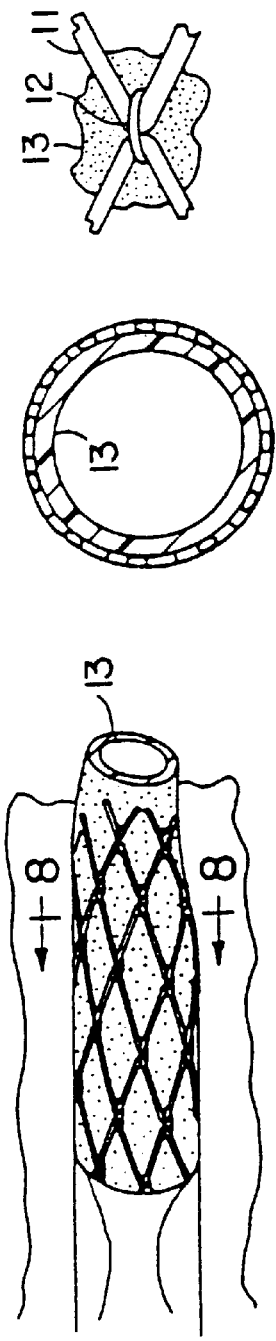
FIG. 7
FIG. 9

INTRALUMINAL STENT AND GRAFT

This is a continuation application of U.S. application Ser. No. 09/251,964, filed Feb. 16, 1999, which is a continuation of U.S. application Ser. No. 09/005,654, filed Jan. 12, 1998 now abandoned, which is a continuation of U.S. application Ser. No. 08/478,181, filed Jun. 7, 1995 now U.S. Pat. No. 5,766,237, which is a division of U.S. application Ser. No. 08/344,524, filed Nov. 23, 1994 now U.S. Pat. No. 5,683,448; which in turn is a continuation of U.S. application Ser. No. 08/025,957, filed Mar. 3, 1993 now abandoned, which in turn is a continuation-in-part of U.S. application Ser. No. 07/839,911, filed Feb. 21, 1992 now U.S. Pat. No. 5,405,377.

BACKGROUND OF THE INVENTION

1. Field of the Invention

The present invention generally relates to a vascular prosthesis, and more particularly to an intraluminal stent which has a flexible and elastic tubular construction with sufficient hoop strength to prevent elastic recoil of balloon-resistant strictures or to produce delayed dilation of those strictures.

2. Description of the Prior Art

The prior art includes a wide variety of intraluminal stents and grafts. For example, Palmaz U.S. Pat. No. 4,733,665 discloses a balloon-expandable intraluminal graft, including an embodiment comprising a wire mesh tube. Intersecting wire members, secured to one another at their intersections by welding, soldering or gluing, form the wire mesh and define a diamond-like pattern. This structure provides a relatively high resistance to radial collapse; but it suffers a number of disadvantages. First it is a rigid structure which cannot easily assume the configuration of a curved vessel which receives it. Second one must use a balloon catheter to expand and implant it. This requirement limits the length of the graft, as does the rigidity.

Other prior stents have more flexible constructions; but they suffer other disadvantages. Wiktor U.S. Pat. No. 4,886,062, for example, discloses a stent which has a relatively flexible construction. This construction includes a deformable wire bent into a zig-zag design and coiled in a spiral fashion. The resulting wire tube has an open configuration with a reduced hoop strength. Each hoop lies essentially isolated from the adjacent hoops and does not obtain substantial support from them. Moreover, the open configuration increases the risk that plaque elements may herniate through the coil. Finally, one must use a balloon catheter to expand and implant it. Thus, the length of the stent cannot exceed the balloon length of available balloon catheters.

The intraluminal stent of the present invention avoids the disadvantages of the prior art stents and grafts. It has sufficient hoop strength to prevent elastic recoil of balloon-resistant strictures. The stent of the present invention has a flexible construction which allows it to follow the curvature of the vessel which receives it. It has an elastic construction which allows implantation without a balloon catheter. This elasticity further allows compression of the structure and recoil upon implantation to produce delayed dilation of the receiving vessel.

SUMMARY OF THE INVENTION

In accordance with an embodiment of the present invention, an intraluminal stent includes a predetermined length of wire having a sinuous or zig-zag configuration and defining a continuous helix with a plurality of connected spirals or hoops. A plurality of loop members connect adjacent apices of adjacent helix hoops. The stent is compressible and self-expandable substantially to the configuration prior to compression.

In accordance with an alternative embodiment of the present invention, an intraluminal stent includes the continuous helix and the plurality of loop members described above. It also includes a prosthetic graft disposed longitudinally of the wire helix within its central opening (or around the wire helix). One or more of the loop members secures the graft to the wire helix. This graft is a flexible, tubular shell which allows the wire helix to contract and recoil.

BRIEF DESCRIPTION OF THE DRAWINGS

For a more complete understanding of this invention one should now refer to the embodiments illustrated in greater detail in the accompanying drawings and described below by way of examples of the invention. In the drawings:

FIG. 5 is a sectional view of the devices used to implant the stent of FIG. 1;

FIG. 6 is a sectional view of the sheath and catheter devices used to implant the stent, showing the catheter holding the stent in place as the sheath moves out of the body vessel.

FIG. 7 is a side elevation view of an alternative embodiment of the stent of the present invention;

FIG. 8 is a sectional view taken along the line 8—8 in FIG. 7;

FIG. 9 is a partial perspective view of the stent of FIG. 7, showing a suture connection for the stent.

While the applicant will describe the invention in connection with preferred and alternative embodiments, one should understand that the invention is not limited to those embodiments. Furthermore, one should understand that the drawings are not necessarily to scale. In certain instances, the applicant may have omitted details which are not necessary for an understanding of the present invention.

DETAILED DESCRIPTION OF THE DRAWINGS

Figure 1:
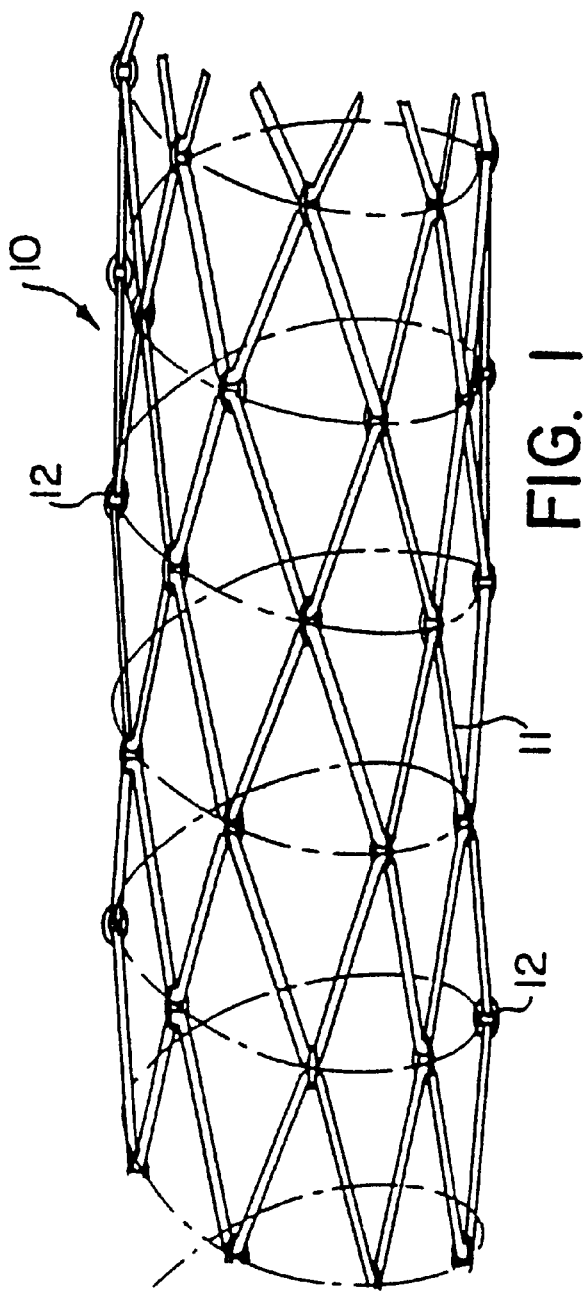
FIG. 1 is a perspective view of the intraluminal stent of the present invention.

Turning now to the drawings, FIG. 1 shows the intraluminal stent of the present invention generally at 10. This stent includes a wire body 11 made out of a predetermined length of wire having a sinuous or zig-sag configuration and defining a continuous helix with a series of connected spirals or hoops. It also includes loop members 12 which connect adjacent apices of adjacent helix hoops to help define the tubular stent. The loop member 12 may connect all or some of the pairs of adjacent apieces.

The wire body 11 is an elastic alloy which provides radial elasticity for the stent. Preferably, it is a nitinol alloy which has superior elasticity and fatigue resistance. The wire has a round cross-section; but its cross-section may also be any one of a variety of shapes, e.g., triangular, rectangular, etc. Alternatively, any material of sufficient strength and elasticity and the other properties identified above may form the wire body, including stainless steel, tantalum, titanium, or any one of a variety of plastics.

Figure 4:
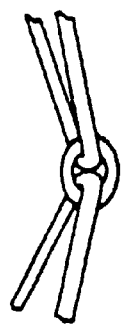
FIGS. 2–4 are side elevation views of a suture connection for the stent of FIG. 1.
Figure 3:
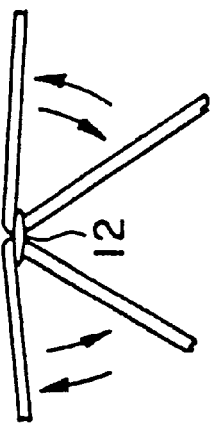
Figure 2:
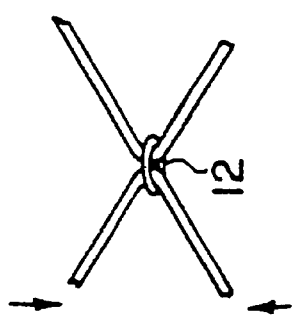

The loop members 12 connect adjacent apices of adjacent hoops of the wire body 11 so that the adjacent apices abut each other (See FIGS. 2–4). Thus, each hoop receives support from adjacent hoops, increasing the hoop strength of the overall stent structure and minimizing the risk of plaque hernitation.

The loop members 12 are ligatures of structure material with the ends tied together to form a loop. This material is polypropylene material or any other biocompatible material of sufficient strenght. Although suture are the preferred connecting means, other connecting means such as staples and rings made of metal or plastic may provide the same function.

The stent structure of the present invention allows compression prior to implantation in a human or animal vessel. After implantation, upon release of the compressive force, the stent structure recoil (or self-expands) to its original configuration. Thus, it continues to provide dilating forces in the implanted state. The structure provides flexibility which allows the stent to follow the curvature of the vessel which receives it.

Turning now to FIGS. 7–9, an alternative embodiment of the present invention includes the wire body arid suture connections described above. This alternatives also includes a prosthetic graft 13 disposed inside the central opening of the wire body. The graft is a round, open tube made of polytetrafluoroethylene (PTFE), dacron or any other suitable biocompatible material. One or more hoop members connect the graft 13 to the wire body 11 as shown in FIG. 9. In place, the graft closes the diamond shaped openings of the stent structure to further minimize plaque herniation and minimize the flow of fluid and cellular elements through the structure.

Alternatively, the graft 13 may lie around the outside of the wire helix. Furthermore, the graft 13 may be co-extensive with the wire helix; or it may be shorter than the wire helix. Finally, the graft 13 may include a plurality of segments disposed within the wire helix or around the outside of the helix.

In one example, the graft 13 is a plain weave fabric construction made in a seamless tubular form on conventional equipment, either a shuttle narrow fabric weaving machine or a needle narrow fabric weaving machine. The tube is of multi filament polyester yarn of 40 denier of less (preferably 20, 30 or 40 denier). The wall thickness of the tube is 0.02 mm or less (preferably 0.1 mm); and it has a water permeability of between 50 and 500 ml/cm$^2$/min at 16 kPa (millimeters of water per square centimeter per minute at a pressure of 16 kPa). The fabric may be coated with a drug substance to reduce permeability, cause local anticoagulation, or reduce cellular infaltration.

Figure 10:
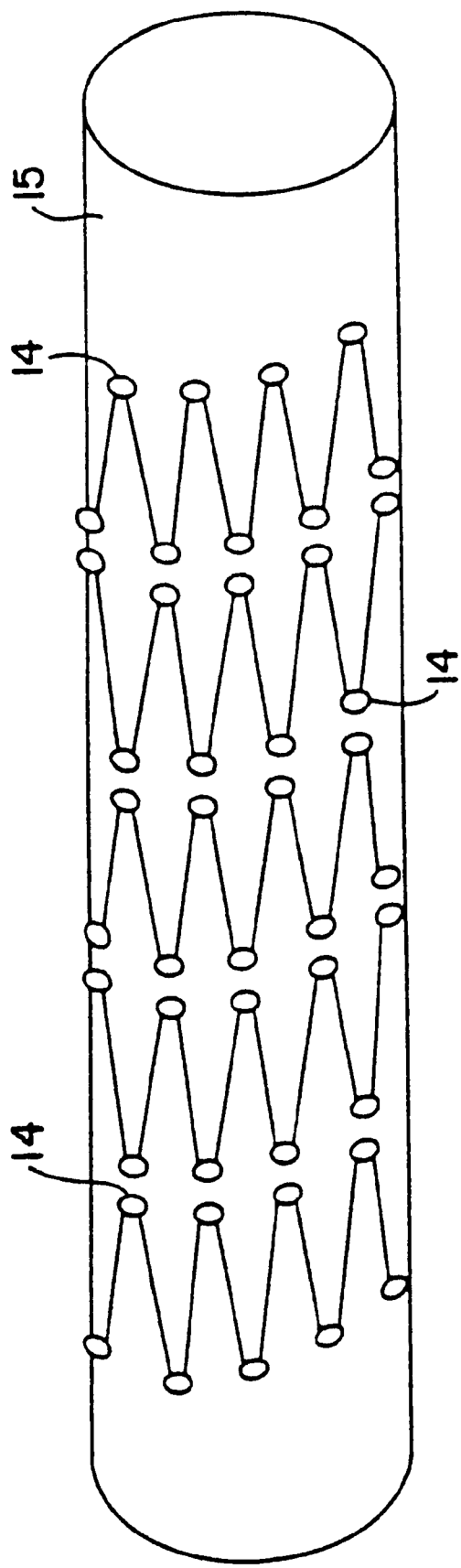
FIG. 10 is a perspective view of the mandrel used to form the wire helix of the present invention.

The method of making the stent of the present invention includes bending a predetermined length of wire in a zig-zag fashion between the pins 14 of the mandrel 15 and around the mandrel, thus forming a helix (See FIG. 10). The next step includes removing the helix from the mandrel by removing the pins and sliding the helix off the mandrel. The process further includes connecting adjacent apices of adjacent helix hoops. A fabricator makes each connection by placing a ligature of suture material (or any other suitable material) around the wire segments which define two adjacent apices and tying the ends of the wire body is nitinol wire, the process includes securing the end of the wire to the mandrel and annealing the wire to a predetermined temperature (and thus imparting a thermal memory for the annealed shape) before removing the helix from the mandrel.

The method of implanting the stem arid graft of the present invention includes compressing it and placing it into the central bare of an introducing device 16. The next step includes coupling the device 16 with the hub 17 of a sheath 18 involves using a catheter 19 to push the compressed stent to the predetermined location and to hold the stent at the location with the catheter, and then removing the sheath. The final step involves removal of the catheter to allow the stent to recall.

In applications in which the wire body is a nitinol metal, a user reduces the diameter of the stent by first cooling it, e.g., by submerging it in ice water. This cooling places the nitinol in a martensitic phase and facilitates manual reduction of the diameter and insertion of the stent in the central bore of the device 16. The device 16 and the sheath 18 restrain the stent until deployment in a predetermined location. At that location in a subject's body fluids warm the nitinol and place it in an austenitic phase which is the stable phase of this metal and which corresponds to a fully opened or expanded configuration of the stent (to its original annealed diameter).

While the above description and the drawings illustrate one embodiment and an alternative, one should understand, of course, that the invention is not limited to those embodiments. Those skilled in the art to which the invention pertains may make other modifications and other embodiments employing the principals of this invention, particularly upon considering the foregoing teachings. For example, one may use a deformable material to construct the wire body 11 of the stent and then use a balloon catheter to deploy it. The applicant, therefore, by the appended claims, intends to cover any modifications and other embodiments which incorporate those features which constitute the essential features of this invention.

What is claimed is:

1. A stent comprising a tubular member having a plurality of hoops aligned adjacent one another along the axis of said tubular member, each of said hoops comprising a plurality of elongate elements, with pairs of said elongate elements meeting one another and forming vertices axially pointing in a direction along the axis of the stent, wherein at least some of said vertices axially abut and are individually connected to oppositely pointed vertices of elongate elements of an adjacent hoop by separated connecting members.

2. A stent according to claim 1, wherein said stent is comprised of a shape memory material.

3. A stent according to claim 2, wherein said shape memory material is nitinol.

4. A stent according to claim 1, wherein said stent is comprised of an elastic material.

5. A stent according to claim 4, wherein said elastic material is stainless steel.

6. A stent according to claim 1, wherein at least one elongate element in each hoop is a continuation of an elongate element of an adjacent hoop.

7. A method of reinforcing a body vessel using a tubular sheath disposed between an entry location in a body and an implantation location, said method comprising the steps of:

a. providing a stent as recited in claim 1;

b. compressing the stent into its compressed configuration;

c. inserting the compressed stent into the tubular sheath;

d. delivering the compressed stent through the tubular sheath to the implantation location; and e. withdrawing the sheath while holding the stent at the implantation location within the vessel and expanding the stent within the implantation location as the sheath is withdrawn by permitting the self-expandable stent, as the constraint of the sheath is removed, to return to said expanded configuration;

whereby the stent is securely disposed in the implanted state against said body vessel.

8. A method according to claim 7, wherein said stent is comprised of a shape memory material.

9. A method according to claim 8, wherein said shape memory material is nitinol.

10. A method according to claim 7, wherein said stent is comprised of an elastic material.

11. A method according to claim 10, wherein said elastic material is stainless steel.

12. A method according to claim 7, wherein at least one elongate element in each hoop is a continuation of an elongate element of an adjacent hoop.

13. A prosthesis for placement in a body lumen comprising a tubular graft supported and adapted to be retained in said lumen by a stent as recited in claim 1.

14. A prosthesis as recited in claim 13 wherein a drug substance is disposed on said tubular graft.

15. Method of implanting a prosthesis at an implementation site in a body lumen comprising providing a stent or a prosthesis as recited in claims 1 or 14, said stent or prosthesis having first and second configurations the diameter of said stent or prosthesis in said first configuration being smaller than in said second configuration, said method comprising introducing said stent or prosthesis, while in its first configuration into a body lumen in communication with said implantation site but remote therefrom, transporting said stent or prosthesis to said implantation site and causing or permitting said stent or prosthesis to assume its second configuration, whereby it is retained at said implantation site.

* * * * *